(12) United States Patent
Cheuvront

(10) Patent No.: US 11,219,410 B2
(45) Date of Patent: Jan. 11, 2022

(54) SYSTEMS AND METHODS FOR ACCURATELY ESTIMATING CUTANEOUS WATER LOSSES IN RESPONSE TO EXERCISE

(71) Applicant: Sports Science Synergy, LLC, Franklin, MA (US)

(72) Inventor: Samuel N. Cheuvront, Franklin, MA (US)

(73) Assignee: SPORTS SCIENCE SYNERGY, LLC, Franklin, MA (US)

( * ) Notice: Subject to any disclaimer, the term of this patent is extended or adjusted under 35 U.S.C. 154(b) by 342 days.

(21) Appl. No.: 16/087,332

(22) PCT Filed: Feb. 21, 2017

(86) PCT No.: PCT/US2017/018627
§ 371 (c)(1),
(2) Date: Sep. 21, 2018

(87) PCT Pub. No.: WO2017/165037
PCT Pub. Date: Sep. 28, 2017

(65) Prior Publication Data
US 2020/0155065 A1 May 21, 2020

Related U.S. Application Data

(60) Provisional application No. 62/310,974, filed on Mar. 21, 2016.

(51) Int. Cl.
*A61B 5/00* (2006.01)
*A61B 5/11* (2006.01)

(52) U.S. Cl.
CPC .......... *A61B 5/4875* (2013.01); *A61B 5/1118* (2013.01); *A61B 5/4266* (2013.01);
(Continued)

(58) Field of Classification Search
CPC ... A61B 5/4875; A61B 5/1118; A61B 5/4266; A61B 5/4866; A61B 2503/10; A61B 2560/0252; A61B 5/7278
See application file for complete search history.

(56) References Cited

U.S. PATENT DOCUMENTS 4,855,942 A 8/1989 Bianco
6,138,079 A 10/2000 Putnam
(Continued)

OTHER PUBLICATIONS

Saltin, B et al. "Body temperatures and sweating during thermal transients caused by exercise." Journal of applied physiology 28 3 (1970): 318-27 (hereinafter—Saltin) (Year: 1970).*
(Continued)

*Primary Examiner* — Devin B Henson
*Assistant Examiner* — Justin Xu
(74) *Attorney, Agent, or Firm* — BakerHostetler

(57) ABSTRACT

A system and method for accurately estimating cutaneous water loss resulting from exercise. The system comprises a component to determine the ambient temperature and a component to determine the total energy expenditure resulting from exercise. The cutaneous water loss is calculated with the equation: Cutaneous Water Loss=(m*(air temperature)+b)*(energy expenditure) where m is a function of air temperature and h is a constant.

20 Claims, 3 Drawing Sheets

(52) U.S. Cl.
CPC ........ *A61B 5/4866* (2013.01); *A61B 2503/10* (2013.01); *A61B 2560/0252* (2013.01)

(56) References Cited

U.S. PATENT DOCUMENTS

| | | | |
|---|---|---|---|
| 6,571,200 | B1 | 5/2003 | Mault |
| 2009/0063090 | A1 | 3/2009 | Surina |
| 2012/0083705 | A1* | 4/2012 | Yuen ...................... G16H 20/30 600/508 |
| 2013/0297220 | A1 | 11/2013 | Yuen et al. |
| 2014/0221792 | A1 | 8/2014 | Miller |
| 2014/0335490 | A1 | 11/2014 | Baarman et al. |
| 2015/0196251 | A1 | 7/2015 | Outwater et al. |
| 2017/0296104 | A1* | 10/2017 | Ryan ...................... G16H 50/30 |

OTHER PUBLICATIONS

International Search Report and Written Opinion dated May 15, 2017 for Application No. PCT/US2017/018627 filed Feb. 21, 2017.
European Search Report dated Sep. 23, 2019 for Application No. 17770782.5 filed Feb. 21, 2017.
Cheuvront et al., "Evaluation of the limits to accurate sweat loss prediction during prolonged exercise", Eur J Appl Physiol. 2007, pp. 215-224.
Gonzalez et al., "Expanded prediction equations of human sweat loss and water needs", J Appl Physiol, 2009, pp. 379-388.
Gonzalez et al., "Sweat rate prediction equations for outdoor exercise with transient solar radiation" J Appl Physiol, Jan. 2012, pp. 1300-1310.
Charkoudian et al., "Planning Military Drinking Water Needs:Development of a User-Friendly Smart Device Application", Military Medicine, 2016, pp. 1142-1150.
Nstitute of Medicine, "Dietary Reference Intakes for Water, Potassium, Sodium, Chloride, and Sulfate", The National Academy Press, Washington, D.C., 2005, 639 pages.
Sawka et al., "Exercise and Fluid Replacement", American College of Sports Medicine, 2007, pp. 377-390.
Cheuvront et al., "Improving the status quo for measuring whole body sweat losses" J Appl Physiol, Jul. 2017, pp. 632-636.
Sollanek et al., "The accurate prediction of sweat rate from energy expenditure and air temperature: a proof-of-concept study", Appl Physiol Nutr Metab., 45, 2020, pp. 1299-1305.
Duking et al., "Comparison of non-invasive individual monitoring of the training and health of athletes with commercially available wearable technologies" Frontiers in Physiology, Mar. 2016, 11 pages.
Coyle et al., BIOTEX—Biosensing Textiles for Personalised Healthcare Management IEEE Trans. Inf. Technol Biomed. vol. 14, Mar. 2010, pp. 364-370.
Havenith et al., "Thermal Indices and Thermophysiological Modeling for Heat Stress", Compr Physiol., Jan. 2016, pp. 255-302.
Shapiro et al., "Predicting Sweat Loss Response to Exercise, Environment and Clothing" Eur J Appl Physiol Occup Physiol, 48, 1982, pp. 83-96.
Barr et al., "Can the endurance athlete get too much of a good thing" Journal of the American Dietetic Association, 89 (11), 1989, pp. 1629-1635.
Cheuvront et al., "Comparison of sweat loss estimates for women during prolonged high-intensity running", Med Sci Sports Exerc. 34(8), Mar. 2002, pp. 1344-1350.
Wickwire et al., "Validation of a Personal Fluid Loss Monitor" Int J Sports Med. Feb. 2008;29(2), pp. 139-144.
Cheuvront et al., "Validation of a Mobile Application Water Planning Tool for Road Race Event Organizers" Med Sci Sports Exerc. May 2019;51(5), pp. 1040-1046.
Cheuvront et al., "Predicted sweat rates for group water planning in sport: accuracy and application" Biology of Sport, vol. 38 No. 2, 2021, pp. 253-260.
Benedict et al., "Insensible Perspiration: Its Relation to Human Physiology and Pathology", Archives of Internal Medicine vol. 38 No. 1, Jul. 1926, 35 pages.
Plnson, "Evaporation from Human Skin with Sweat Glands Inactivated", From the Departments of Physiology and Pediatrics, The University of Rochester School of Medicine and Dentistry, Rochester, N.Y, Jun. 5, 1942, 12 pages.
Stolwijk et al., "Physiological Factors Associated with Sweating During Exercise", Aerospace Medicine, Oct. 1968, pp. 1101-1105.
Almond et al., "Hyponatremia Among Runners in the Boston Marathon", N Engl J Med 352;15, Apr. 14, 2005, pp. 1550-1556.
Byrne et al., "Continuous Thermoregulatory Responses to Mass-Participation Distance Running in Heat", Official Journal of the American College of Sports Medicine, Dec. 2005, pp. 803-810.
Magazanik et al., "Enzyme Blood Levels and Water Balance During a Marathon Race", Journal of Applied Physiology vol. 36, No. 2, Feb. 1974, pp. 214-217.
Cohen et al., "Changes in Serum Electrolyte Levels During Marathon Running", SA Medical Journal, Mar. 1978, 5 pages.
Adams et al., "Thermoregulation During Marathon Running in Cool, Moderate, and Hot Environments" Jounal of Applied Physiology vol. 38, No. 6, Jun. 1975, pp. 1030-1037.
Maron et al., "Acute Blood Biochemical Alterations in Response to Marathon Running", Europ. J. appl. Physiol. 34, Mar. 1975, pp. 173-181.
Maron et al., "Thermoregulatory Responses During Competitive Marathon Running", J. Appl. Physiol.: Respirat. Environ. Exercise Physiol. 42(6): 1977, pp. 909-914.
Cheuvront et al., "Ad libitum fluid intakes and thermoregulatory responses of female distance runners in three environments" Journal of Sports Sciences, 2001, 19, pp. 845-854.
Myhre et al., "Plasma Volume Changes in Middle-Aged Male and Female Subjects During Marathon Running", J. Appl. Physiol. 59(2), 1985, pp. 559-563.
Myhre et al., "Plasma Volume and Blood Metabolites in Middle-Aged Runners During a Warm-Weather Marathon", Eur J Appl Physiol 48, 1982, pp. 227-240.
Pugh et al., "Rectal Temperatures, Weight Losses, and Sweat Rates in Marathon Running", J. Appl. Physiol. 23(3), 1967, pp. 347-352.
Brown et al., "Thermoregulation During Prolonged Actual and Laboratory-Simulated Bicycling", Eur J Appl Physiol 54, 1985, pp. 125-130.
Maughan et al., "Water alnd Salt Balance of Well-Trained Swimmers in Training" Internatin Journal of Sport Nutrition and Exercise Metabolism 19, 2009, pp. 598-606.
Lemon et al., "Urea Production During Prolonged Swimming" Jounal of Sports Sciences, 7, 1989, pp. 241-246.
Saunders et al., "The Effects of Different Air Velocities on Heat Storage and Body Temperature in Humans Cycling in a Hot, Humid Environment", Acta Physiol Scand 183, 2005, pp. 241-255.
Fox et al., Thermal and Fluid Balance in Competitive Cycling, American College of Sports Medicine, Board #82, May 2013, One page.
O'Neal et al., "Hydration Profile and Influence of Beverage Contents on Fluid Intake by Women During Outdoor Recreational Walking", Eur J Appl Physiol 112, 2012, pp. 3971-3982.
Kurdak et al., "Hydration and Sweating Responses to Hot-Weather Football Competition" Scand J Med Sci Sports 20 Suppl 3, 2010, pp. 133-139.
Maughan et al., "Water Balance and Salt Losses in Competitive Football", International Journal of Sport Nutrition and Exercise Metabolism 17, 2007, pp. 583-594.

* cited by examiner

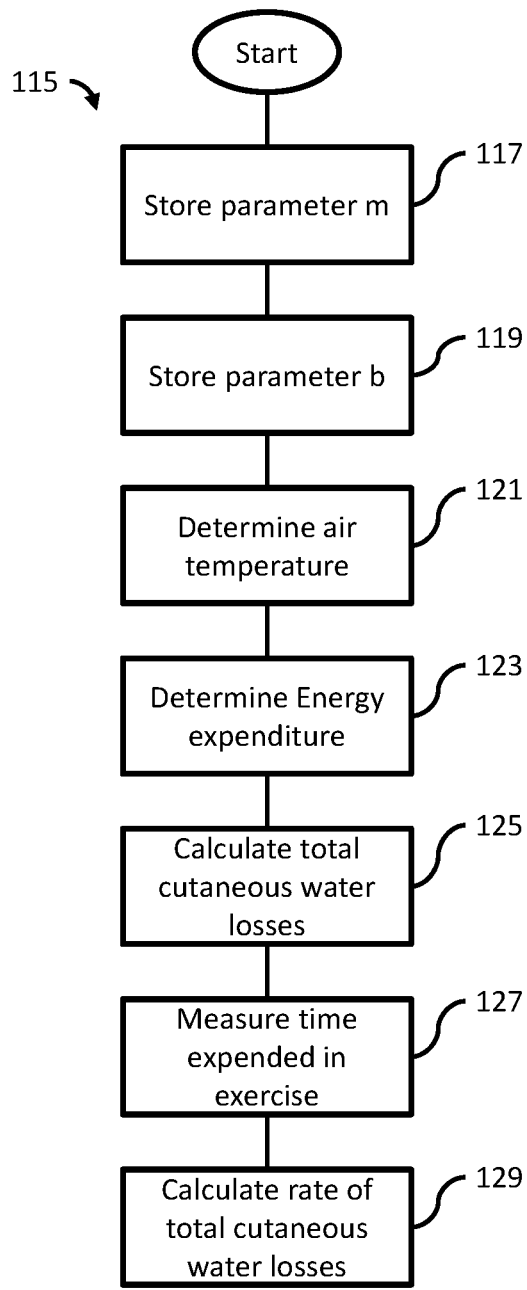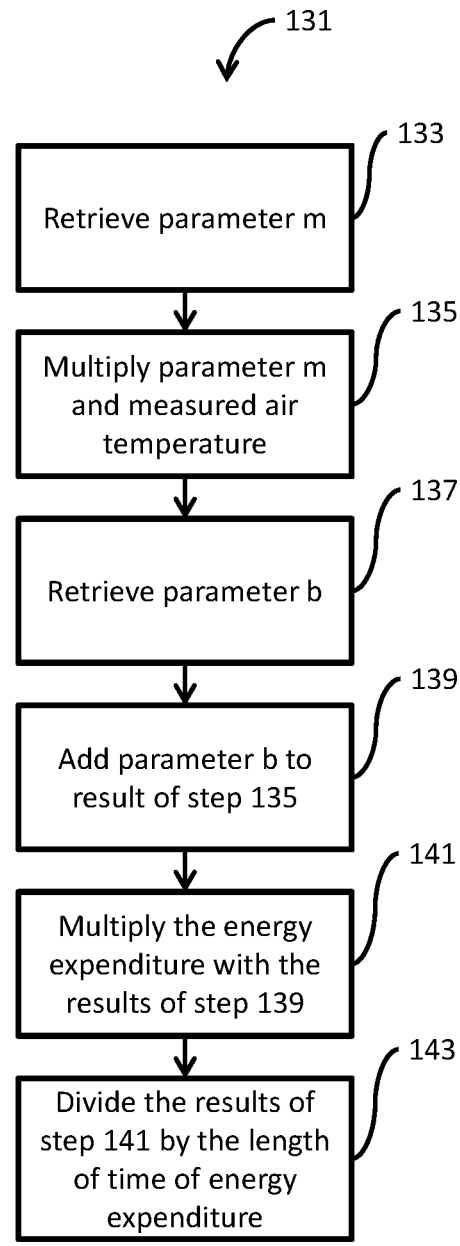
FIG. 3
FIG. 4

SYSTEMS AND METHODS FOR ACCURATELY ESTIMATING CUTANEOUS WATER LOSSES IN RESPONSE TO EXERCISE

CROSS-REFERENCE TO RELATED APPLICATIONS

This application is the National Stage Application of International Patent Application No. PCT/US2017/018627, filed Feb. 21, 2017, which claims the benefit of U.S. Provisional Patent Application No. 62/310,974 filed Mar. 21, 2016 and entitled SYSTEMS AND METHODS FOR ACCURATELY ESTIMATING CUTANEOUS WATER LOSSES IN RESPONSE TO EXERCISE which are hereby incorporated by reference herein.

TECHNICAL FIELD

This invention relates to accurately estimating water losses from the skin in response to exercise by use of an equation that integrates air temperature and energy expenditure alone as required inputs.

BACKGROUND

Human water losses occur through cutaneous insensible evaporation and sensible perspiration, respiration, and through body waste elimination (urine and feces). Cutaneous evaporative water losses are commonly referred to as sweat, though only sensible losses are truly secreted from sweat glands while insensible losses evaporate directly from the skin. During physical labor, exercise, or exposure to hot environments, cutaneous water losses increase in association with endogenous (metabolism) and exogenous (environmental) heat gain. Body water losses can be substantial and must be replaced. There is considerable variation in water losses among people owing to biological and environmental factors, thus fluid needs vary considerably also. Avoidance of over-drinking and under-drinking are strongly recommended to optimize health and performance by avoiding hyponatremia and dehydration, respectively. As a result, it is also strongly recommended that athletes and exercise enthusiasts know their individual rates of cutaneous water loss for a given set of circumstances and tailor drinking behaviors accordingly.

The precise measurement of cutaneous water losses can be made in a laboratory by gravimetric means combined with appropriate corrections for non-cutaneous losses of mass (respiratory water and $CO_2$—$O_2$ exchange). Simple changes in nude mass can be used as an approximate surrogate, but failure to also account for fluid intake and urine output confounds the accuracy of nude weights. Prolonged activities and activities that require comparatively large amounts of energy per unit weight and distance covered (e.g., swimming) especially benefit by additional correction for non-cutaneous mass losses. 'Sweat' prediction equations have been developed and published to help estimate exercise body water losses independent of the need to measure fluid losses or fluid gains, but only one has been integrated into a device to compute individual water losses in real time (U.S. Pat. No. 6,138,079) and none have been validated for use with athletes to assure that estimates do not produce significant risk of over-drinking (hyponatremia) or under-drinking (dehydration).

Energy expenditure and air temperature represent potential endogenous and exogenous sources of body heat gain, respectively. Together these two variables increase the uncertainty of water needs due to their influence on water losses. Knowledge of individual energy expenditure may solve much of the variation problem that limits accurate estimation of individual exercise water losses. Many different state-of-the-art wearable sensors have been developed to accurately track energy expenditure to this end. The strong modifying effects of air temperature on exercise water losses can also be addressed by simple use of a weather 'app' to estimate local area air temperatures. The present invention computes individual cutaneous water losses associated with exercise by integrating a simple thermo-physiological equation with any third party parameters of measured or acquired air temperature and measured energy expenditure. The output is independent of common measurement confounders (e.g., fluid intake, urine output) and is pre-corrected for non-cutaneous mass losses.

There are several different equations residing in the public domain which can be used to estimate body water losses during exercise. None of the equations available to athletes have been validated for accuracy. Only one device (U.S. Pat. No. 6,138,079) on the market today claims to provide athletes with a way of computing losses or rates at which water must be replenished during exercise.

U.S. Patent Application Publication No. 2014/0221792 discloses a hydration monitoring apparatus. The hydration monitoring apparatus comprises a data acquisition unit, an analysis unit, a sensor interface, a data communication unit, a display and an input output interface. In individuals, biometric, biological, and/or physiological status can be monitored in real time by using sensors. The data collected from the sensors are analyzed separately in combination using multimodal analysis of multivariate analysis to determine an individual's hydration level or dehydration state. The data collected may include the individual's heart rate. The accuracy of the apparatus is unknown.

U.S. Pat. No. 6,138,079 discloses a device for calculating the amount of water being lost through dehydration. Personal data such as weight is entered into the device at the start of exercise. The device calculates from the specified weight as well as the measured outdoor temperature and humidity the average loss of fluid. The accuracy of the device is unknown.

There is a need for a simple and accurate system and method for calculating cutaneous water loss as a result of exercise.

SUMMARY

The inventions satisfy the aforementioned needs in the art by providing systems and methods for measuring cutaneous water loss as a result of exercise. The method includes the steps of determining the air temperature, measuring the energy expended during exercise, multiplying the air temperature with a parameter m to obtain a first result adding the first result to a parameter b to obtain a second result and multiplying the second result with the energy expended during exercise.

In accordance with another embodiment of the invention, a system for calculating the cutaneous water loss resulting from exercise is provided. The system includes a computer system comprising at least one processor, a component for determining ambient temperature, a component for determining the energy expended during exercise, and an application that when executed by the processor computes cutaneous water loss as a function of the ambient temperature and the energy expended during exercise.

BRIEF DESCRIPTION OF THE DRAWINGS

FIG. 3 is a flow diagram of a method of measuring total cutaneous water losses and the rate of total cutaneous water losses.

FIG. 4 is a flow diagram of a method for calculating total cutaneous water losses and the rate of total cutaneous water losses using parameters m and b.

DETAILED DESCRIPTION OF ILLUSTRATIVE EMBODIMENTS

Figure 1:
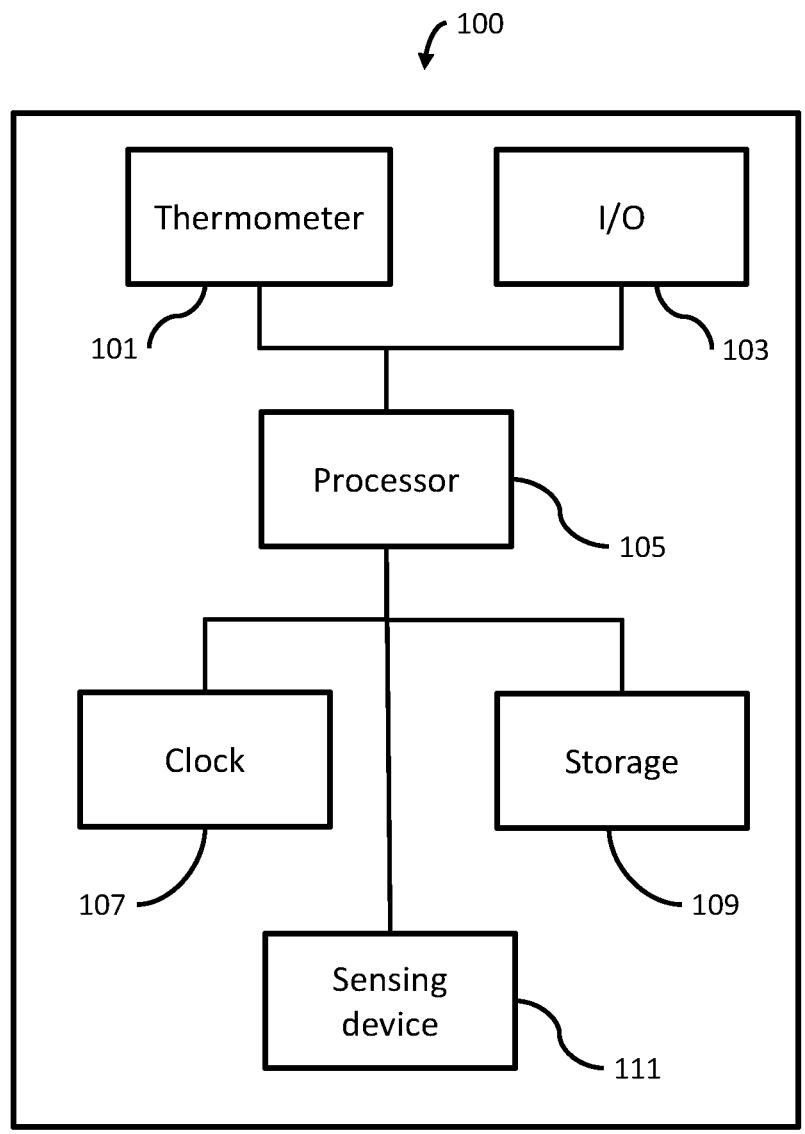
FIG. 1 is a schematic of a device for measuring cutaneous water loss due to exercise.

Illustrated in FIG. 1 is a device 100 for measuring total cutaneous water losses as a result of exercise. The device 100 may include a temperature determining component 101, and input output component 103, a processor 105, the clock 107, a storage device 109 and an energy expenditure sensing device 111.

The temperature determining component 101 may be a thermometer to measure ambient temperature, or an application to download ambient temperature based on location.

A number of devices have been described that measure energy expenditure during exercise. For example, U.S. Pat. No. 4,855,942, Title: Pedometer and/or Calorie Measuring Device and Method (Bianco, Aug. 8, 1989), describes a device with a number of calories consumed by subject performing an exercise routine is approximated with a computer having a predetermined cycle time during which the distance traveled by the subject is determined. U.S. Pat. No. 6,571,200, titled: Monitoring Caloric Expenditure Resulting from Body Activity (Mault, May 27, 2003), discloses an apparatus for monitoring the caloric expenditure rate of the subject comprising a caloric expenditure rate detector for detecting and measuring the caloric expenditure rate of the subject; a body activity detector for detecting and measuring the body activity of the subject; and a processor for storing a measured caloric expenditure rate and a concurrently measured body activity for each of a plurality of different body activities and activity rates, to enable each subsequently detected body activity measurement to be converted to the caloric expenditure rate of the respective subject.

For example, energy expenditure sensing device 111 may comprise a caloric expenditure rate detector for detecting and measuring the caloric expenditure rate of the person exercising. The caloric expenditure rate detector may include a body activity detector that may detect physical activities of the subject including walking, and running at different rates and/or physical exertions of the subject such as for example the heart rate of the subject. Other sensors have been developed to measure the caloric expenditure during exercise. Some sensors convert mechanical energy output to calories consumed by the person exercising. Other sensors measure the pulse rate and estimate the calorie totals using a pre-constructed relationship between the user's heart rate and calories burned across the individual's entire heart rate range.

Another method of calculating energy expenditure is to provide a sensor that measures the number of times that a cyclically moving member (e.g. an arm) moves during exercise. This may be implemented as a pedometer with a number of pulses is directly proportional to the number of steps taken by the subject. Calories are calculated in response to an input from a pedometer, as well as preset inputs indicative of subject age, weight and sex. Calories are determined from an approximately linear relationship of the number of calories burned by a subject having a known weight moving, by walking, jogging or running, through a predetermined distance. The linear relationship between calories burned and weight can be approximated as:

(Calories burned)=$a$*(Distance)+$c$ where a and c are predetermined constants which vary according to the sex of the subject.

Yet another method of calculating exercise energy expenditure is to use metabolic equivalent (MET) values in accordance with the following formula:

Exercise Energy Expenditure=(MET)(Weight)(Duration)

MET values have been calculated for a variety of activities such as bicycling, calisthenics, rowing, running, and the like. MET values of activities range from 0.9 (sleeping) to 23 (running at 22.5 km/h or a 4:17 mile pace). Thus the exercise energy expenditure may be determined by multiplying the product of weight and duration of the exercise with the MET value for that exercise.

Another method of calculating exercise energy expenditure is to determine a distance traveled by a subject during a predetermined period of time $t_1$; inputting a weight for the subject W1; accessing a measure of the number of calories expended per unit weight and time F for the exercise; and calculating the energy expended E in accordance with the formula:

$E=(t_1)(W1)(F)$.

In the present inventions, it has been determined that cutaneous water loss can be estimated by using the air temperature and energy expenditure in accordance with the following formula:

($m$*(air temperature)+$b$)*(energy expenditure)=Cutaneous Water Loss.

The biophysics and physiology of heat transfer were used to arrive at water losses in mL/kcal, which was then regressed against air temperature in degrees C. Numerous values for cutaneous water loss (mL/kcal) and air temperature coordinates for a small theoretical universe of conditions were established by using a multitude of basic biophysics, physiology, and exercise science terms and calculations including those in the public domain. The slope (m) and intercept term (b) are outputs from linear regression analysis. Those parameters are the key to ultimately allowing simple implementation of very complex information. The relationship between y and x for running (cycling, walking, swimming, soccer, etc.) just happens to be best fit by a straight line, so y=mx+b is the best mathematical fit. This therefore produces a linear equation with slope (m) and intercept (b) terms. The slope is multiplied by air temperature and the intercept is added. The parameter m is a function of air temperature and the parameter b is a constant term. The answer is water loss in mL/kcal. Simply multiply by total energy expenditure and you get total water loss. Divide by time an you get the rate of water loss. If exercise duration is <60 min, the mL/kcal solution to the thermo-physiological equation should be divided by the time constant for sweating, before calculating sweating rate, to account for the fact that sweating does not begin instantaneously at the onset of exercise. Failure to account for the delay contributes non-significantly when exercise duration is >60 min.

The parameters m and b may be estimated by measuring the cutaneous water loss ($WL_1$) resulting from an exercise at an ambient temperature ($T_1$), measuring the cutaneous water loss ($WL_2$) resulting from the exercise at an ambient temperature ($T_2$), estimating the amount of energy expended (E) during the exercise and solving for m and b using the equation:

$$m=((WL_1-WL_2)/E)/(T_1-T_2)$$

and $$b=(WL_2/E)-(((WL_1-WL_2)/E)/(T_1-T_2))(T_2).$$

The generalized equation above will be the same for walking, cycling, and even swimming. The only thing that will change is the parameter m and the constant b. Similarly, the same generalized equation can be adapted for use in team sports, group water planning, and can even be adjusted to include additional inputs (using multiple linear regression) to improve equation performance when the desired test conditions fall outside the original equation domain of validity.

Cutaneous water losses are a function of endogenous (muscle metabolism) and exogenous (environmental) heat gain. Transcutaneous (non-sweat) water loss from the skin increases in response to metabolism and environmental temperature. Thermoregulatory sweating increases as a function of changes in body core (Tc) and skin temperatures (Ts) (Stolwijk, et al., 1968). The measurement of these variables is impractical and inconvenient outside of a research laboratory. However, relationships among these variables are generally linear and can be reasonably approximated by more convenient measurements or even estimates. For example, changes in Tc can be approximated by heat production, which can be approximated by energy expenditure. This is especially true when normalized for body mass. Ts can be approximated by environmental temperature. Therefore, cutaneous water losses in response to exercise can be theoretically approximated by knowledge of energy expenditure and environmental temperature alone.

A small theoretical universe of conditions was created from which cutaneous water losses were approximated. The conditions included a range of realistic body mass (60 to 90 kg), body surface area (1.68 to 2.08 $m^2$), running speed (140 to 280 m/min) and environmental air temperature (10 to 35° C.) combinations. Relative humidity was varied from 35 to 75% depending on air temperature and assuming a daily reciprocal cycle between air temperature and relative humidity. The associated range of air water vapor pressures was 6.91 to 14.81 mm Hg. The theoretical requirement for evaporative cooling was set to less than 70% of the maximum evaporative capacity of the environment (i.e., Ereq/Emax<0.70), thus evaporative efficiency was assumed to be high. More humid conditions require a third vapor pressure term (multiple regression) and can be used to predict cutaneous water losses with Ereq/Emax between 0.71 and 1.10. The theoretical running distance was set to 42 km. Any clothing worn under these conditions in the real world would vary greatly, thus clothing was left out of the analysis entirely and accepted as a source of potential error. Cutaneous water losses were estimated by concatenating standard biophysical equations of heat balance and energy expenditure within an Excel® spreadsheet. Most quantitative relationships among variables of interest were obtained from the open literature. In situations where no quantitative equation existed relating variables of interest to this analysis, equations were developed de novo. From this master file of equations and conditions, cutaneous water loss output was generated per unit energy expenditure (mL/kcal) and ultimately related to air temperature (° C.) by forcing function. A final, single thermo-physiological equation was created which can be used to estimate cutaneous water losses when only air temperature and energy expenditure are known.

Figure 2:
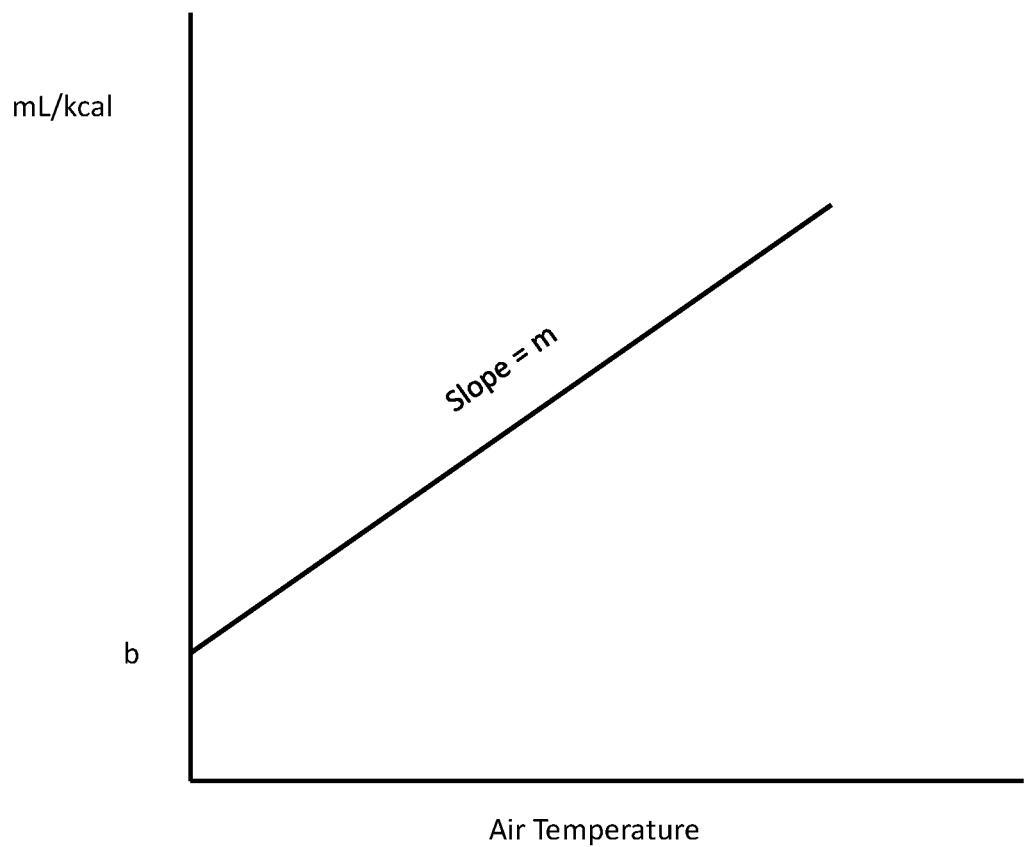
FIG. 2 is a generalized graph showing the relationship of air temperature and cutaneous water loss per kilocalorie.

FIG. 2 is a generalized graph illustrating the relationship between ambient temperature and cutaneous water loss per calorie of energy expended. Parameters m and b may be calculated by measuring the cutaneous water losses during exercise at a first temperature, and the energy expended by that subject during such exercise; and measuring the cutaneous water losses during exercise at a second temperature, and the energy expended by that subject during such exercise. Those measurements will provide two data points which are sufficient to algebraically solve the linear equation for parameter m and constant b. The precise values for m and b will be slightly different for each person. A line of best fit has been developed to provide a single m and b value that works "for everybody" within the acceptable designated error limits.

Accuracy, Validation, and Comparisons

The inherent equation error is <55 mL/L/1000 kcal of energy expenditure, thus it is entirely negligible when compared to the resolution of most medical scales used to measure whole body sweating rates in the field. In order to test the estimation validity of the thermo-physiological equation, 10 studies were identified and compiled from the open literature where body water loss rates (L/h) were carefully measured and reported from changes in body mass during prolonged outdoor running exercise or indoor running exercise (treadmill) with realistic convective airflow (Table 1). For studies that did not correct for non-cutaneous losses of body mass, a standardized correction was subtracted from the reported whole body losses, expressed per unit energy expenditure (i.e., g/kcal). From the 10 studies, 109 individual observations of the required inputs were obtained (Table 2) except energy expenditure, which was estimated from the same standard equations used in the Excel® file. The thermo-physiological equation was compared to two other equations published in the open literature (Barr and Costill, 1989) or in patent form (Putnam, 2000) (Table 2). Other equations based on heat balance parameters, though commonly adopted in occupational or military settings, were not evaluated for several reasons. Briefly, they require many inputs (i.e., ≥10) including several which are commonly unknown, such as clothing insulation and vapor permeability characteristics. More importantly, the conditions under which athletes and recreational enthusiasts exercise can be well outside the domain of validity for said equations, thus greatly limiting their use, application, and validity for sport.

TABLE 1

Research studies used to compare and
validate equation performance (running).

| Research Study (first author name, journal, year of publication) | # individual observations |
|---|---|
| Adams et al. Journal of Applied Physiology (1975) | 13 |
| Byrne et al. Medicine and Science in Sports & Exercise (2006) | 18 |
| Cheuvront et al. Journal of Sports Sciences (2001) | 24* |
| Cohen et al. South African Medical Journal (1978) | 18 |
| Magazanik et al. Journal of Applied Physiology (1974) | 6 |
| Maron et al. European Journal of Applied Physiology (1975) | 6 |
| Maron et al. Journal of Applied Physiology (1977) | 6 |
| Myhre et al. European Journal of Applied Physiology (1982) | 3 |
| Myhre et al. Journal of Applied Physiology (1985) | 11 |
| Pugh et al. Journal of Applied Physiology (1967) | 4 |
| TOTAL | 109 |

*Paper reports group means; individual data obtained from Cheuvront dissertation, Florida State University (2000).

Table 2 lists the equations compared in the analysis as well as their required inputs.

TABLE 2

Equations for estimating rates of body water loss during exercise.

| Authors | Equation | Inputs |
|---|---|---|
| Barr & Costill, 1989 | $\dfrac{kg \times \dfrac{km}{h}}{720}$ | body mass; running speed |
| Putnam, 2000 | $\dfrac{METS \times kg \times Ta + rh2}{1450}$ | METS, body mass, air temperature; square of relative humidity |
| Applicant's invention | $\dfrac{(m(\text{air temperature}) + b) \times \text{energy expenditure}}{\text{time}}$ | air temperature, energy expenditure, time (if rate is desired) |

All equation outputs normalized to L/h units for comparison.

Equation accuracy was examined and compared in two ways. The first was by assigning an acceptable 'absolute' estimation error rate of ±0.250 L/h. This threshold was chosen based on the desire for a total volume error rate of ≤1.0 L/4 hours. For a smaller athlete (~50 kg), ±1.0 L/4 h would increase or decrease body mass by ±2% over 4 hours of continuous exercise, increasing the health and performance risks of hyponatremia and dehydration, respectively (Almond et al., 2005; Sawka et al., 2007). Although these are conservative estimates that guard against health and performance risks during exercise conducted over 4 hours, they become even more important as athletic events become increasingly protracted (i.e., ultra-endurance events) and when there is a negative balance between sweat electrolyte losses and electrolyte consumption. Performance was assessed using the mean absolute difference (MAD) in order to appreciate the magnitude of the error on the mean without regard for sign or directionality. Individual error was assessed by simply counting the number of over-estimates (hyponatremia risk), under-estimates (dehydration risk), and the total number of estimation errors (total risk). The odds of estimating cutaneous water losses correctly (within ±0.250 L/h) were calculated as (proportion correct/1−proportion correct): 1.

The second way of testing equation accuracy was to apply an acceptable 'relative' estimation error of ±2% for calculated gains or losses of actual body mass (as body water). Estimated rates of cutaneous water loss were subtracted from observed rates of exercise body water losses reported in the literature (Table 1), multiplied by the duration of exercise, then divided by actual body mass and expressed as a percentage of mass gain or loss (Table 1). An acute 2% loss of body mass (as water) is a conservative threshold for the start of measurably impaired performance due to dehydration (Sawka et al., 2007). An acute 2% gain in body mass (as water) is a conservative threshold for the development of symptomatic hyponatremia (Almond et al., 2005). This second approach is more liberal since errors of 0.250 L/h or more may not appreciably increase risk in larger individuals (>50 kg) who exercise for durations <4 hours. Performance was assessed using the MAD in order to appreciate the magnitude of the error on the mean without regard for sign or directionality. The odds of estimating cutaneous water losses correctly (within ±2% body mass) were calculated as (proportion correct/1−proportion correct): 1.

Table 4 provides the results of equation performances compared to a conservative absolute error rate threshold of ±0.250 L/h. Only the equation disclosed herein met the MAD criteria. The overall odds of a correct estimate for the equation disclosed herein were 2.34:1 (70% probability of correctness). The odds and probabilities for Barr and Costill (1989) and Putnam (2000) were 0.8:1 (44% probability of correctness) and 1.3:1 (58% probability of correctness), respectively.

TABLE 4

Evaluation of absolute equation performance (±0.250 L/h threshold).

| Equation | MAD (L/h) | Dehydration Risk Error | Hyponatremia Risk Error | Total Risk Error | Odds of Correct Estimate |
|---|---|---|---|---|---|
| Barr & Costill, 1989 | 0.302 | 20/109 | 43/109 | 61/109 | 0.8:1 |
| Putnam, 2000 | 0.258 | 3/109 | 43/109 | 46/109 | 1.37:1 |
| Applicant's invention | 0.188* | 17/109 | 16/109 | 33/109 | 2.3:1 |

*= acceptable performance

Table 5 provides the results of equation performances compared to a liberal relative error threshold of ±2% body mass. All three equations met the MAD criteria for the more liberal threshold. The overall odds of a correct estimate for the equation disclosed herein were 12.5:1 (93% probability of correctness). The odds and probabilities for Barr and Costill (1989) and Putnam (2000) were 2.6:1 (72% probability of correctness) and 4.4:1 (82% probability of correctness), respectively.

TABLE 5

Evaluation of relative equation performance (±2% body mass threshold).

| Equation | MAD (% body mass) | Dehydration Risk Error | Hyponatremia Risk Error | Total Risk Error | Odds of Correct Estimate |
|---|---|---|---|---|---|
| Barr & Costill, 1989 | 1.45%* | 15/109 | 15/109 | 30/109 | 2.6:1 |
| Putnam, 2000 | 1.26%* | 1/109 | 19/109 | 20/109 | 4.4:1 |
| Applicant's invention | 0.92%* | 8/109 | 3/109 | 11/109 | 12.5:1 |

*= acceptable performance

The Applicant's thermo-physiological equation is valid for the data set tested, which includes primarily outdoor running (or treadmill running with adequate airflow) at measured running speeds ranging from 145 to 268 m/min, distances run from 15 to 42 km, duration of running from 60 min to 280 min, air temperatures from 10 to 35° C., body weights ranging from 41.6 to 88.3 kg, and measured cutaneous water loss rates of 0.38 to 2.11 L/h.

Adjustments of the parameters m and b of the equation for outdoor walking, cycling, and swimming exercise have also been developed. A small theoretical universe of conditions was created once again and cutaneous water losses were approximated as with running. The conditions were identical to those for running except that for cycling the movement speeds ranged from 286 to 572 m/min. For walking, movement speeds ranged from 80.4 to 127 m/min. Swimming velocity was 30 to 60 m/min in water temperatures ranging from 26 to 28° C. Inherent equation errors were larger than for running (<55 mL/kcal) but still small at 118 mL (walking), 207 mL (cycling) and 64 mL/1000 kcal (swimming), respectively. Validation data are limited to a handful of studies reporting only group mean rates of water loss for outdoor cycling, walking, and swimming exercise. Once corrected for non-cutaneous losses of mass (respiratory water and $CO_2$—$O_2$ exchange), the applicant's equation estimated water losses within ±0.250 L/h in 6 out of 6 studies examined (Table 6).

TABLE 6

Research studies used to compare and validate equation performance (walking, cycling, or swimming). Data are from reported group means.

| Research Study (first author name, journal, year of publication) | MAD (L/h) |
|---|---|
| Brown et al., European Journal of Applied Physiology (1985)-cycling | −0.173* |

TABLE 6-continued

Research studies used to compare and validate equation performance (walking, cycling, or swimming). Data are from reported group means.

| Research Study (first author name, journal, year of publication) | MAD (L/h) |
|---|---|
| Lemon et al., Journal of Sports Sciences (1989)-swimming | −0.185* |
| Saunders et al., Acta Physiologica Scandinavica (2005)-cycling | −0.039* |
| Maughan et al., International Journal of Sport Nutrition and exercise Metabolism (2009)-swimming (men) | 0.061* |
| Maughan et al., International Journal of Sport Nutrition and exercise Metabolism (2009)-swimming (women) | 0.022* |
| O'Neal et al., European Journal of Applied Physiology (2012) | 0.053* |
| Fox and Burns, Thermal and fluid balance in competitive cycling, DeSales University (2013) | 0.148* |

*acceptable performance (±0.250 L/h).

An adaptation for soccer was validated similarly whereby 5 out of 6 estimated group means were predicted within ±0.250 L/h (Table 7).

TABLE 7

Research studies used to compare and validate equation performance for soccer. Data are from reported group means.

| | |
|---|---|
| Maughan et al., International Journal of Sport Nutrition and Exercise Metabolism (2007)-Team A | −0.272 |
| Maughan et al., International Journal of Sport Nutrition and Exercise Metabolism (2007)-Team B | −0.216* |
| Kurdak et al., Scandinavian Journal of Medicine and Science in Sports (2010)-Team W1 | −0.064* |
| Kurdak et al., Scandinavian Journal of Medicine and Science in Sports (2010)-Team S1 | −0.163* |

TABLE 7-continued

Research studies used to compare and validate equation performance for soccer. Data are from reported group means.

| | |
|---|---|
| Kurdak et al., Scandinavian Journal of Medicine and Science in Sports (2010)-Team W2 | −0.005* |
| Kurdak et al., Scandinavian Journal of Medicine and Science in Sports (2010)-Team S2 | −0.099* |

*acceptable performance (±0.250 L/h).

Illustrated in FIG. 3 is a method 115 of measuring total cutaneous water losses.

In step 117 parameter m is stored in a device memory. In some embodiments a plurality of values for m (e.g. $m_1$, $m_2$, ... $m_n$) may be stored wherein each value for m corresponds to a particular type of exercise (e.g. swimming, cycling, walking, etc.).

In step 119 parameter b is stored in the device memory. In some embodiments a plurality of values for b (e.g. $b_1$, $b_2$, ... $b_n$) may be stored wherein each value for b corresponds to a particular type of exercise (e.g. swimming, cycling, walking, etc.).

In step 121 the air temperature is determined. The air temperature may be determined by measuring the air temperature or by downloading a measured air temperature from a website that provides air temperature by location.

In step 123 the energy expenditure of an individual is measured. Indirect assessment of energy expenditure may be obtained by heart-rate recording. In any individual, there is a relationship between heart rate and oxygen consumption, and this relationship is the basis for the monitoring of physical activity by recording heart rate over lengthy periods of time. However, it is also well known that the relationship between heart rate and energy expenditure will vary within the individual, depending upon the type of physical activity being undertaken. Other methods of measuring energy expenditures may include the use of an ergometer, a device which measures the amount of work performed, such as for example an indoor rower calibrated to measure the amount of energy being generated. Other devices for measuring physical activity include pedometers and accelerometers. These would be attached to the body to detect motion and provide an estimate of total activity.

In step 125 the total cutaneous water loss is calculated using the air temperature, the energy expenditure, parameter m and parameter b.

In step 127 the rate of total cutaneous water loss may be calculated by dividing the total cutaneous water loss by the length of time of exercise.

FIG. 4 is a flowchart diagram illustrating the method of calculation 131 of the cutaneous water loss during exercise.

In step 133 the value of parameter m is retrieved from memory.

In step 135 parameter m is multiplied by the air temperature to obtain a first result.

In step 137 the value of parameter b is retrieved from memory.

In step 139 the value of parameter b is added to the first result from step 135 to obtain a second result.

In step 141 the energy expenditure is multiplied by the second result from step 139 to provide the total cutaneous water loss.

In step 143 the total cutaneous water losses divided by the length of time of energy expenditure.

It should be noted, that the steps described for FIG. 3 and FIG. 4 do not have to be performed in order and that all the steps have to be performed in order or out of order to achieve the results of the invention. The device 100 may be a personal computer (PC), a UNIX workstation, a server, a mainframe computer, a personal digital assistant (PDA), smartphone, cellular phone, a tablet computer, a laptop computer, a netbook, a slate computer, or some combination of these. Further in accordance with various embodiments of the invention, the methods described herein are intended for operation with dedicated hardware implementations including, but not limited to, PCs, PDAs, semiconductors, application specific integrated circuits (ASIC), programmable logic arrays, cloud computing devices, and other hardware devices constructed to implement the methods described herein. The computing devices described herein include standard components such as a processor/controller, a memory, a display, input/output devices (keyboard, mouse, etc.), communication bus, connections (USB, Serial, Wireless), software including operating systems and predictive and forecasting techniques and the like, a camera, power supply and the like.

It should also be noted that the software implementations of the invention as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the invention is considered to include a tangible storage medium or distribution medium, as listed herein and including art-recognized equivalents and successor media, in which the software implementations herein are stored. The software described herein may be part of one software module and are not required to be separate.

Communication media generally embodies computer-readable instructions, data structures, program modules or other data in a modulated signal such as the carrier waves or other transportable mechanism including any information delivery media. Computer-readable media such as communication media may include wireless media such as radio frequency, infrared microwaves, and wired media such as a wired network. Also, the computer-readable media can store and execute computer-readable codes that are distributed in computers connected via a network. The computer readable medium also includes cooperating or interconnected computer readable media that are in the processing system or are distributed among multiple processing systems that may be local or remote to the processing system. The invention can include the computer-readable medium having stored thereon a data structure including a plurality of fields containing data representing the techniques of the invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES

1. Benedict F G, Root H F. Insensible perspiration: Its relation to human physiology and pathology. Archives of Int Med 38: 1-35, 1926.

2. Pinson, E A. Evaporation from human skin with sweat glands inactivated. American Journal of Physiology, 137: 492-503, 1942.
3. Stolwijk J A J, Saltin B, Gagge A P. Physiological factors associated with sweating during exercise. Aerospace Med Oct: 1101-1105, 1968.
4. Barr, S I, Costill, D L. Water: Can the endurance athlete get too much of a good thing? Journal of the American Dietetic Association, 89(11): 1629-1635, 1989.
5. Almond, C S D, Shin A Y, Fortescue E B, Mannix R C, Wypij D, Binstadt B A, Duncan C N, Olson D P, Salerno A E, Newburger J W, Greenes D S. Hyponatremia among runners in the Boston Marathon. New England Journal of Medicine, 352:1550-1556, 2005.
6. Sawka, M N, Burke, L M, Eichner, E R, Maughan, R J, Montain, S J, Stachenfeld, N S. Exercise and fluid replacement. Medicine and Science in Sports and Exercise, 39: 377-390, 2007.

What is claimed:

1. A system comprising:
at least one sensor configured to determine sensor data; and
at least one processor configured to:
determine an air temperature for a location associated with an exercise performed by a subject;
determine, based on the sensor data, an energy expended during the exercise;
determine a first result based on the air temperature and a first constant (m);
determine a second result based on combining the first result and a second constant (b);
determine a cutaneous water loss based on multiplying the second result and the energy expended during the exercise; and
cause output of data indicative of the cutaneous water loss,
wherein one or more of the first constant or the second constant are estimated based on a universe of conditions for a plurality of subjects, and wherein at least one condition of the universe of conditions is assigned a range of values used for estimating one or more of the first constant or the second constant.

2. The system of claim 1, wherein the at least one processor is configured to combine the first result with the second constant (b) by adding the first result to the second constant (b).

3. The system of claim 1, wherein the first constant (m) is calculated by measuring a cutaneous water loss ($WL_1$) resulting from an exercise at an ambient temperature ($T_1$), measuring a cutaneous water loss ($WL_2$) resulting from the exercise at an ambient temperature ($T_2$), estimating an amount of energy expended (E) during the exercise, and solving for the first constant (m) using the equation:

$$m = ((WL_1 - WL_2)/E)/(T_1 - T_2)$$

4. The system of claim 2, wherein the second constant (b) is calculated by measuring a cutaneous water loss ($WL_1$) resulting from an exercise at an ambient temperature ($T_1$), measuring a cutaneous water loss ($WL_2$) resulting from the exercise at an ambient temperature ($T_2$), estimating an amount of energy expended (E) during the exercise, and solving for the second constant (b) using the equation:

$$b = (WL_2/E) - (((WL_1 - WL_2)/E)/(T_1 - T_2))(T_2)$$

5. The system of claim 1, wherein the at least one processor is configured to determine the energy expended during the exercise by estimating the energy expended from one or more of a heart rate sensor, a pedometer, or an accelerometer.

6. The system of claim 1, wherein the at least one processor is configured to determine the energy expended during the exercise by:
determining a distance traveled by the subject during a predetermined period of time ($t_1$);
inputting a weight ($W_1$) for the subject;
accessing a measure (F) of a number of calories expended per unit weight and time for the exercise; and
calculating the energy expended (E) in accordance with the formula:

$$E = (t_1)(W_1)(F).$$

7. A method of calculating cutaneous water loss of a subject, the method comprising:
determining an air temperature for a location associated with an exercise performed by a subject;
determining an energy expended (E) during the exercise;
determining a first result based on the air temperature and a first constant (m);
determining a second result based on combining the first result and a second constant (b);
determining a cutaneous water loss based on multiplying the second result and the energy expended during the exercise; and
causing output of data indicative of the cutaneous water loss,
wherein one or more of the first constant or the second constant are estimated based on a universe of conditions for a plurality of subjects, and wherein at least one condition of the universe of conditions is assigned a range of values used for estimating one or more of the first constant or the second constant.

8. The method of claim 7, wherein the first constant (m) and the second constant (b) are estimated by measuring a cutaneous water loss ($WL_1$) resulting from an exercise at an ambient temperature ($T_1$), measuring a cutaneous water loss ($WL_2$) resulting from the exercise at an ambient temperature ($T_2$), estimating an amount of energy expended (E) during the exercise, and solving for the first constant (m) and the second constant (b) using the equations:

$$m = ((WL_1 - WL_2)/E)/(T_1 - T_2)$$

and $$b = (WL_2/E) - (((WL_1 - WL_2)/E)/(T_1 - T_2))(T_2)$$

9. The method of claim 7, wherein the determining the energy expended during the exercise comprises estimating the energy expended from one or more of a heart rate sensor, a pedometer, or an accelerometer.

10. The method of claim 7, wherein the determining the energy expended during the exercise comprises:
determining a distance traveled by the subject during a predetermined period of time ($t_1$);
inputting a weight ($W_1$) for the subject;
accessing a measure (F) of a number of calories expended per unit weight and time for the exercise; and
calculating the energy expended (E) in accordance with the formula:

$$E = (T_1)(W_1)(F).$$

11. The method of claim 7, wherein the determining the energy expended (E) during the exercise comprises:
determining a metabolic equivalent (MET) for the exercise;

inputting a weight (W) of the subject;
measuring a duration of the exercise; and
calculating E in accordance with the following formula:

$$E=(MET)(W)(Duration).$$

12. A non-transitory computer readable medium storing computer-executable instructions that, when executed, cause:
- determining an air temperature for a location associated with an exercise performed by a subject;
- determining an energy expended during the exercise;
- determining a first result based on the air temperature and a first constant (m);
- determining a second result based on combining the first result and a second constant (b);
- determining a cutaneous water loss based on multiplying the second result and the energy expended during the exercise; and
- causing output of data indicative of the cutaneous water loss,
- wherein one or more of the first constant or the second constant are estimated based on a universe of conditions for a plurality of subjects, and wherein at least one condition of the universe of conditions is assigned a range of values used for estimating one or more of the first constant or the second constant.

13. The non-transitory computer readable medium of claim 12, wherein the first constant (m) and the second constant (b) are estimated by measuring a cutaneous water loss ($WL_1$) resulting from the exercise at an ambient temperature ($T_1$), measuring a cutaneous water loss ($WL_2$) resulting from the exercise at an ambient temperature ($T_2$), estimating an amount of energy expended E during the exercise, and solving for the first constant (m) and the second constant (b) using the equations:

$$m=((WL_1-WL_2)/E)(T_1-T_2)$$

and $$b=(WL_2/E)-(((WL_1-WL_2)/E)/(T_1-T_2))(T_2).$$

14. The non-transitory computer readable medium of claim 12, wherein the step of determining the energy expended during the exercise comprises estimating the energy expended from one or more of a heart rate sensor, a pedometer, or an accelerometer.

15. The non-transitory computer readable medium of claim 12, wherein the determining the energy expended during the exercise comprises:
- determining a distance traveled by the subject during a predetermined period of time ($t_1$);
- inputting a weight ($W_1$) for the subject;
- accessing a measure (F) of a number of calories expended per unit weight and time for the exercise; and
- calculating the energy expended (E) in accordance with the formula:

$$E=(t_1)(W_1)(F).$$

16. The non-transitory computer readable medium of claim 12, wherein the determining the energy expended (E) during exercise comprises:
- determining a metabolic equivalent (MET) for the exercise;
- inputting a weight (W) of the subject;
- measuring a duration of the exercise; and
- calculating E in accordance with the following formula:

$$E=(MET)(W)(Duration).$$

17. The system of claim 1, wherein the universe of conditions are indicative of one or more exercises performed in a range of conditions by the plurality of subjects having a range of physical characteristics.

18. The system of claim 1, wherein at least a portion of the universe of conditions are specific to a type of exercise performed by the subject.

19. The method of claim 7, wherein the first constant and the second constant are applicable to determining cutaneous water loss for each of a plurality of different subjects.

20. The method of claim 7, wherein the universe of conditions comprises one or more of a range of air temperatures in which the exercise is performed, a range of distances for performing the exercise, a range of durations for performing the exercise, a range of body characteristics of the plurality of subjects, or a range of speeds for performing the exercise.

* * * * *

UNITED STATES PATENT AND TRADEMARK OFFICE
CERTIFICATE OF CORRECTION

PATENT NO. : 11,219,410 B2
APPLICATION NO. : 16/087332
DATED : January 11, 2022
INVENTOR(S) : Samuel N. Cheuvront It is certified that error appears in the above-identified patent and that said Letters Patent is hereby corrected as shown below:

On the Title Page

Item (57) ABSTRACT:
Line 8, delete "*h*" and insert -- *b* --.

Signed and Sealed this
Eleventh Day of July, 2023

Katherine Kelly Vidal
*Director of the United States Patent and Trademark Office*